United States Patent [19]

Barbachyn et al.

[11] Patent Number: 5,688,792
[45] Date of Patent: Nov. 18, 1997

[54] SUBSTITUTED OXAZINE AND THIAZINE OXAZOLIDINONE ANTIMICROBIALS

[75] Inventors: Michael R. Barbachyn, Kalamazoo; Steven J. Brickner, Portage; Douglas K. Hutchinson, Kalamazoo, all of Mich.

[73] Assignee: Pharmacia & Upjohn Company, Kalamazoo, Mich.

[21] Appl. No.: 617,877

[22] PCT Filed: Aug. 16, 1994

[86] PCT No.: PCT/US94/08904

§ 371 Date: Mar. 5, 1996

§ 102(e) Date: Mar. 5, 1996

[87] PCT Pub. No.: WO95/07271

PCT Pub. Date: Mar. 16, 1995

[51] Int. Cl.⁶ .................................................. A61K 31/535
[52] U.S. Cl. ........................... 514/235.5; 514/236.8; 544/137
[58] Field of Search ................ 544/137; 514/236.8, 514/235.5

[56] References Cited

U.S. PATENT DOCUMENTS

| | | | |
|---|---|---|---|
| 4,348,393 | 9/1982 | Bourgery et al. | 424/248.57 |
| 4,801,600 | 1/1989 | Wang et al. | 514/376 |
| 4,921,869 | 5/1990 | Wang et al. | 514/376 |

FOREIGN PATENT DOCUMENTS

| | | |
|---|---|---|
| 127902 | 12/1984 | European Pat. Off. |
| 184170 | 6/1986 | European Pat. Off. |
| 312000 | 10/1988 | European Pat. Off. |
| 316594 | 10/1988 | European Pat. Off. |
| 352781 | 1/1990 | European Pat. Off. |
| WO90/02744 | 5/1990 | WIPO |
| WO93/09103 | 5/1993 | WIPO |
| WO93/23384 | 11/1993 | WIPO |

OTHER PUBLICATIONS

Gregory, W.A., et al., J. Med. Chem., 32, 1673–81 (1989).

Primary Examiner—Mukund J. Shah
Assistant Examiner—Michael Bucknum
Attorney, Agent, or Firm—Donald L. Corneglio; Martha A. Gammill

[57] ABSTRACT

A compound of structural Formula I:

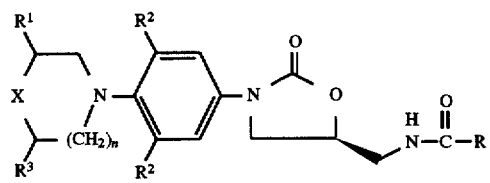

or pharmaceutically acceptable salts thereof wherein:

X is O, S, SO, $SO_2$, $SNR^{10}$ or $S(O)NR^{10}$;

R is (a) hydrogen,
(b) $C_1$–$C_8$ alkyl optionally substituted with one or more of the following: F, Cl, hydroxy, $C_1$–$C_8$ alkoxy, $C_1$–$C_8$ acyloxy or —O—$CH_2$—Ph,
(c) $C_3$–$C_6$ cycloalkyl,
(d) amino,
(e) $C_1$–$C_8$ alkylamino,
(f) $C_1$–$C_8$ dialkylamino or
(g) $C_1$–$C_8$ alkoxy;

$R^1$ is H, except when X is O then $R^1$ can be H, $CH_3$, CN, $CO_2H$, $CO_2R$ or $(CH_2)_m R^{11}$ (m is 1 or 2);

$R^2$ is independently H, F or Cl;

$R^3$ is H except when X is O and $R^1$ is $CH_3$ then $R^3$ can be H or $CH_3$;

$R^{10}$ is independently H, $C_1$–$C_4$ alkyl (optionally substituted with chloro, fluoro, hydroxy, $C_1$–$C_8$ alkoxy, amino, $C_1$–$C_8$ alkylamino, or $C_1$–$C_8$ dialkylamino) or p-toluenesulfonyl;

$R^{11}$ is hydrogen, OH, OR, OCOR, $NH_2$, NHCOR or $N(R^{10})_2$; and n is 0, 1 or 2. The oxazine and thiazine oxazolidinone derivatives are useful antimicrobial agents, effective against a number of human and veterinary pathogens, including gram-positive aerobic bacteria such as multiply-resistant staphylococci, streptococci and enterococci as well as anaerobic organisms such as *Bacteroides spp.* and *Clostridia spp.* species, and acid-fast organisms such as *Mycobacterium tuberculosis*, *Mycobacterium avium* and *Mycobacterium spp.*

12 Claims, No Drawings

SUBSTITUTED OXAZINE AND THIAZINE OXAZOLIDINONE ANTIMICROBIALS

BACKGROUND OF THE INVENTION

The subject invention discloses oxazine and thiazine oxazolidinone derivatives. The compounds are useful antimicrobial agents, effective against a number of human and veterinary pathogens, including gram-positive aerobic bacteria such as multiply-resistant staphylococci, streptococci and enterococci as well as anaerobic organisms such as *Bacteroides spp.* and *Clostridia spp.* species, and acid-fast organisms such as *Mycobacterium tuberculosis*, *Mycobacterium avium* and *Mycobacterium spp.*

INFORMATION DISCLOSURE

The present compounds are similar to piperazine containing ring structures such as those disclosed in the publications below except that the distal nitrogen atom is replaced with an oxygen, sulfur, sulfinyl, sulfonyl, sulfimidoyl or sulfonimidoyl. The instant compounds are unique in that typically the unsubstituted piperazinyl oxazolidinone compounds have little useful antibacterial activity whereas the activity observed for the corresponding oxazine and thiazine derived oxazolidinones is high.

PCT/US93/03570 application discloses oxazolidinones containing a substituted diazine moiety and their uses as antimicrobials.

PCT/US92/08267 application discloses substituted aryl and heteroaryl-phenyl-oxazolidinones useful as antibacterial agents.

PCT/US89/03548 application discloses 5'indolinyl-5β-amidomethyloxazolidinones, 3-(fused-ring substituted)phenyl-5β-amidomethyloxazolidinones, and 3-(nitrogen substituted)phenyl-5β-amidomethyloxazolidinones which are useful as antibacterial agents.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF THE INVENTION

In one aspect the subject invention is a compound of structural Formula I:

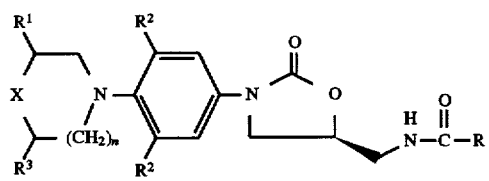

or pharmaceutically acceptable salts thereof wherein:
X is O, S, SO, $SO_2$, $SNR^{10}$ or $S(O)NR^{10}$;
R is (a) hydrogen, (b) $C_1$–$C_8$ alkyl optionally substituted with one or more of the following: F, Cl, hydroxy, $C_1$–$C_8$ alkoxy, $C_1$–$C_8$ acyloxy or O—$CH_2$—Ph,
(c) $C_3$–$C_6$ cycloalkyl,
(d) amino,
(e) $C_1$–$C_8$ alkylamino,
(f) $C_1$–$C_8$ dialkylamino, or
(g) $C_1$–$C_8$ alkoxy;

$R^1$ is H, except when X is O then $R^1$ can be H, $CH_3$, CN, $CO_2H$, $CO_2R$ or $(CH_2)_m R^{11}$ (m is 1 or 2);

$R^2$ is independently H, F or Cl;

$R^3$ is H except when X is O and $R^1$ is $CH_3$ then $R^3$ can be H or $CH_3$;

$R^{10}$ is independently H, $C_1$–$C_4$ alkyl (optionally substituted with chloro, fluoro, hydroxy, $C_1$–$C_8$ alkoxy, amino, $C_1$–$C_8$ alkylamino or $C_1$–$C_8$ dialkylamino) or -p-toluenesulfonyl;

$R^{11}$ is hydrogen, OH, OR, OCOR, $NH_2$, NHCOR or $N(R^{10})_2$; and n is 0, 1 or 2.

Preferred compounds where n is 0 are:
(a) (S)-N-[[3-[3-fluoro-4-(3-thiazolidinyl)phenyl]-2-oxo-5-oxazolidinyl]methyl]acetamide;
(b) (S)-N-[[3-[3-fluoro-4-(1,1-dioxothiazolidin-3-yl)phenyl]-2-oxo-5-oxazolidinyl]methyl]acetamide;
(c) (S)-N-[[3-[3-fluoro-4-(1-oxothiazolidin-3-yl)phenyl]-2-oxo-5-oxazolidinyl]methyl]acetamide; or
(d) (S)-N-[[3-[3-fluoro-4-(3-oxazolidinyl)]phenyl]-2-oxo-5-oxazolidinyl]methyl]acetamide.

Preferred compounds where n is 1 are:
(a) (S)-N-[[3-[3-fluoro-4-(4-thiomorpholinyl)phenyl]-2-oxo-5-oxazolidinyl]methyl]acetamide;
(b) (S)-N-[[3-[3-fluoro-4-(1,1-dioxothiomorpholin-4-yl)phenyl]-2-oxo-5-oxazolidinyl]methyl]acetamide;
(c) (S)-N-[[3-[3-fluoro-4-(1-oxothiomorpholin-4-yl)phenyl]-2-oxo-5-oxazolidinyl]methyl]acetamide;
(d) (S)-N-[[3-[3,5-difluoro-4-morpholinyl]phenyl]-2-oxo-5-oxazolidinyl]methyl]acetamide;
(e) (S)-N-[[3-[3-fluoro-4-morpholinyl]phenyl]-2-oxo-5-oxazolidinyl]methyl]acetamide;
(f) (S)-N-[[3-[3-fluoro-4-[1-[(p-toluenesulfonyl)imino]thiomorpholin-4-yl]phenyl]-2-oxo-5-oxazolidinyl]methyl]acetamide;
(g) (S)-N-[[3-[3-fluoro-4-morpholinyl]phenyl]-2-oxo-5-oxazolidinyl]methyl]hydroxyacetamide;
(h) (S)-N-[[3-[3-fluoro-4-morpholinyl]phenyl]-2-oxo-5-oxazolidinyl]methyl]formamide;
(i) (S)-N-[[3-[3-fluoro-4-morpholinyl]phenyl]-2-oxo-5-oxazolidinyl]methyl]methylcarbamate; or
(j) (S)-N-[[3-[3-fluoro-4-morpholinyl]phenyl]-2-oxo-5-oxazolidinyl]methyl]dichloroacetamide.

Preferred compounds where n is 2 are:
(a) (S)-N-[[3-[3-fluoro-4-(hexahydrothiazepin-4-yl)phenyl]-2-oxo-5-oxazolidinyl]methyl]acetamide;
(b) (S)-N-[[3-[3-fluoro-4-(1,1-dioxohexahydrothiazepin-4-yl)phenyl]-2-oxo-5-oxazolidinyl]methyl]acetamide;
(c) (S)-N-[[3-[3-fluoro-4-(1-oxohexahydrothiazepin-4-yl)phenyl]-2-oxo-5-oxazolidinyl]methyl]acetamide; or
(d) (S)-N-[[3-[3-fluoro-4-(hexahydrooxazepin-4-yl)]phenyl]-2-oxo-5-oxazolidinyl]methyl]acetamide.

In another aspect, the subject invention is directed toward a method for treating microbial infections in patients by administering to a patient in need thereof an effective mount of a compound of Formula I as described above. The compound can be administered in a pharmaceutical composition either orally, parenterally or topically. Preferably, the compound is administered in an amount of from about 0.1 to about 100 mg/kg of body weight/day, more preferably, from about 3.0 to about 50 mg/kg of body weight/day.

DETAILED DESCRIPTION OF THE INVENTION

The present invention discloses oxazine and thiazine oxazolidinones of structural Formula I as defined above. The compounds are useful antimicrobial agents, effective against a number of human and veterinary pathogens, particularly gram-positive aerobic bacteria such as multiply-resistant staphylococci, streptococci and enterococci as well as anaerobic organisms such as *Bacteroides spp.* and *Clostridia spp.* species, and acid-fast organisms such as *Mycobacterium tuberculosis, Mycobacterium avium* and *Mycobacterium spp.*

The carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus, $C_1$-$C_3$ alkyl refers to alkyl of 1–3 carbon atoms, inclusive, or methyl, ethyl, propyl, and isopropyl; $C_1$-$C_8$ alkyl is methyl, ethyl, propyl, butyl, pentyl, hexyl, heptyl, octyl and isomeric forms thereof.

The term $C_1$-$C_8$ alkylamino means an amino moiety (—NH—) containing one alkyl moiety having 1 to 8 carbon atoms. The term $C_1$-$C_8$ dialkylamino means an amino moiety containing two alkyl moieties having 1 to 8 carbon atoms, for example, propylamino and dipropylamino respectively. The $C_1$-$C_8$ alkyl or $C_1$-$C_4$ alkyl groups can be optionally substituted with chloro, fluoro, hydroxy, $C_1$-$C_8$ alkoxy, amino, $C_1$-$C_8$ alkylamino, $C_1$-$C_8$ dialkylamino or —O—CH$_2$Ph where "Ph" is phenyl. "Acyloxy" are groups such as methylcarbamate, ethylcarbamate,etc. Such optionally substituted $C_1$-$C_8$ alkyl groups can include 1-chloropropyl, 1-fluoroprepyl 3-chloropropyl, 3-fluoro propyl, 1-hydroxy butyl, 2-hydroxy butyl, 1-methoxypropyl, 1-octyloxy propyl, 1-amino propyl, 1-aminooctyl, 1-butylaminopropyl, 1-dibutylaminopropyl and the like.

Pharmaceutically acceptable salts means acid addition salts useful for administering the compounds of this invention and include hydrochloride, hydrobromide, hydroiodide, surfate, phosphate, acetate, propionate, lactate, mesylate, maleate, malate, succinate, tartrate, citric acid, 2-hydroxyethyl sulfonate, fumarate and the like when a basic group is present. These salts may be in hydrated form.

The benzene ring, in addition to being unsubstituted, can be substituted with one or more halogen atoms in the series fluorine or chlorine. Thus, the $R^2$ groups can be independently either hydrogen atoms or halogen atoms in a variety of substitution patterns.

The $R^2$ substituents are preferably both fluorine and, more preferably, fluorine and H.

The preferred absolute configuration at C-5 of the oxazolidinone ring of compounds claimed in this invention is as represented in the structure of Formula I. This absolute configuration is called (S) under the Cahn-Ingold-Prelog nomenclature system. It is this (S)-enantiomer which is antibacterially active. The racemic mixture is useful in the same way and for the same purpose as the pure (S)-enantiomer, the difference is that twice as much racemic material must be used to produce the same antibacterial effect. It will be apparent to one skilled in the art that appropriate modifications to the morpholine or thiomorpholine ring systems of compounds of Formula I, for example the incorporation of a second chiral center ($R^1$ not H), will lead to diastereomers. These diastereomers, in racemic and enantiomerically enriched forms, are also within the scope of the compounds of Formula I of the invention.

Optically pure material could be obtained either by resolution from a racemic mixture by selective crystallization of a diastereomeric salt from, for example, an intermediate amine with an appropriate optically active acid such as dibenzoyl tartrate or 10-camphorsulfonic acid, followed by treatment with base to afford the optically pure amine.

The preferred method of preparation of oxazolidinones of Formula I in enantiomerically pure form is depicted in Charts 1 and 2.

As shown in Chart 1, oxazines and thiazines such as thiazolidine ($R^1$=H, X=S, n=0), oxazolidine ($R^1$=H, X=O, n=0), morpholine ($R^1$=H, X=O, n=1), thiomorpholine ($R^1$= H, X=S, n=1), a substituted morpholine ($R^1$ not H, X=O, n=1), hexahydro-1,4-thiazepine ($R^1$=H, X=S, n=2), hexahydro-1,4-oxazepine ($R^1$=H, X=O, n=2), or a substituted hexahydro-1,4-oxasepine ($R^1$ not H, X=O, n=2) of structure 1 are reacted with a functionalized nitrobenzene 2 (Y=halogen or trifluoromethanesulfonate) in the presence of a suitable base such as N,N-diisopropylethylamine and in a suitable solvent such as acetonitrile, tetrahydrofuran (THF) or ethyl acetate at reflux temperature to provide the adducts 3. When necessary, the $R^1$ sidechain of 1 is protected with a suitable protecting group(s) such as a benzyl or other variants as described in Greene, T. W.; Wuts, P. G. M. "Protective Groups in Organic Synthesis", 2nd ed.; John Wiley & Sons: New York (1991) which is removed later in the synthesis. When X=O, the nitro group of 3 is then reduced by hydrogenation in the presence of a suitable catalyst such as palladium on carbon (hydrogen supplied in the form of a gas or indirectly via ammonium formate) in a suitable solvent such as ethyl acetate, tetrahydrofuran, methanol and mixtures thereof. Alternatively, and preferably in the case where X=S, the nitro group of 3 can be reduced by the action of aqueous sodium hydrosulfite in tetrahydrofuran at ambient temperature to give the anilines 4. The anilines 4 are then converted to their benzyl ($R^4$=CH$_2$Ph) or methyl ($R^4$=CH$_3$) urethane derivatives 5, employing standard Schotten-Baumann conditions or other variations known to one skilled in the art. The urethanes 5 are then deprotonated with a suitable base such as n-butyllithium or LiN(SiMe$_3$)$_2$ in a suitable solvent such as tetrahydrofuran ("THF") and at a suitable temperature such as −78° to −40° C. to give a lithiated intermediate which is then treated with commercially available (−)-(R)-glycidyl butyrate. Warming to ambient temperature then directly affords the hydroxymethyl-substituted oxazolidinones 6 in enantiomerically enriched form. Compound 6 is then converted to the corresponding mesylate 7 ($R^5$=methanesulfonyl) or aryl sulfonate 7 ($R^5$=ArSO$_2$, for example p-toluenesulfonyl) by the action of, for example, methanesulfonyl chloride/pyridine or methanesulfonyl chloride/triethylamine/dichloromethane or p-toluenesulfonyl chloride/pyridine. The resultant sulfonate derivative 7 is then reacted with an azide source such as sodium or potassium azide in an aprotic solvent such as N,N-dirnethylformamide (DMF) or 1-methyl-2-pyrrolidinone optionally in the presence of a catalyst such as 18-crown-6 at a temperature of 50°–90 ° C. to afford the azide 8 ($R^6$=N$_3$). The azide is then reduced by hydrogenation with palladium on carbon or a platinum catalyst in an appropriate solvent such as ethyl acetate or methanol to give the corresponding amine 8 ($R^6$=NH$_2$).

Alternatively, the azide can be reduced by treatment with a trivalent phosphorus compound such as triphenylphosphine in a suitable solvent such as tetrahydrofuran followed by the addition of water. Alternatively, the mesylate or aryl sulfonate can be displaced with potassium phthalimide in acetonitrile at reflux or other suitable solvent. The phthalimide 8 ($R^6$=phthalimide) is then deprotected by the addition of aqueous methyl amine in refluxing ethanol, to give the amine 8 ($R^6$=$NH_2$). Alternatively, the amine 8 may be obtained directly from mesylate 7 by treatment with ammonium hydroxide by refluxing in isopropanol or THF. The amine 8 is then acylated by reactions known to those skilled in the art to give oxazolidinones of structure 9. For example, the amine can be reacted with an acid chloride or anhydride in a basic solvent such as pyridine at a temperature ranging from −30° to 30° C. to provide the acylated compound 9 (R=optionally substituted alkyl). It will be apparent to one skilled in the art that other acyl groups within the scope of this invention can be readily appended to the amine 8 ($R^6$=$NH_2$) by standard acylation techniques, for example, those highlighted in March, J. "Advanced Organic Chemistry", 3rd ed.; John Wiley & Sons: New York, 1985; p 370–375, to give additional examples of 9. At this juncture, any appended protecting group on the $R^1$ sidechain of the branched morpholine or hexahydro-1,4-oxazepine congeners (X =O ) is removed, where applicable, employing appropriate conditions such as those noted in Greene, T. W.; Wuts, P. G. M., "Protective Groups in Organic Synthesis," 2nd ed.; John Wiley & Sons: New York (1991). The compounds of structure 9 represent examples of oxazine- and thiazine-substituted oxazolidinone antibacterial agents of Formula I, which are the subject of this invention.

As shown in Chart 2, the thiazolidine-containing or thiomorpholine-containing oxazolidinones 10 (and also the hexahydro-1,4-thiazepine-containing variants), themselves examples of antibacterial agents of Formula I, can be further elaborated to additional compounds of Formula I as shown in Chart 2. Specifically, 10 can be oxidized to the corresponding sulfoxides 11 (X=sulfinyl) with sodium metaperiodate in a mixture of water and methanol. In addition, compounds 10 or 11 can be oxidized to the sulfones 12 (X=sulfonyl) by treatment with oxone or 4-methylmorpholine N-oxide and catalytic osmium tetroxide in aqueous acetone. Sulfides 10 can also be converted to sulfilimines 13 (X=sulfimidoyl). For example, treatment of 10 with chloramine-T trihydrate in dichloromethane in the presence of a suitable phase transfer catalyst such as hexadecyltributyl- phosphonium bromide affords compounds 13 ($R^{10}$=p-toluenesulfonyl). Additional sulfilimines can be prepared by methods known to one skilled in the art, for example, those disclosed in Oae, S.; Furukawa, N. "Sulfilimines and Related Derivatives"; American Chemical Society: Washington, D.C., 1983. Sulfoximine derivatives 14 (X=sulfonimidoyl) are also accessible by further elaboration of the sulfoxides 11 and sulfilimines 13. Numerous methods and variations for these transformations are available: (1) Johnson, C. R., "Comprehensive Organic Chemistry"; Jones, N., ed.; Pergamon Press: Oxford, 1979; Vol. 3, Chapter 11.11, (2) Johnson, C. R., *Aldrichimica Acta*, 1985, 18, 3–4 and references cited therein, (3) Johnson, C. R.; Lavergne, O., *J. Org. Chem.* 1989, 54, 986–988 and references cited therein, (4) Johnson, C. R.; Rigau, J. J., *J. Org. Chem.* 1968, 33, 4340–4343, and (5) Oae, S.; Furukawa, N., "Sulfilimines and Related Derivatives"; American Chemical Society: Washington, D.C., 1983; p 297–317 and references cited therein. For example, oxidation of N-tosylsulfilimines 13 ($R^{10}$=p-toluenesulfonyl) with aqueous sodium hypochlorite in a mixture of ethyl acetate and dichloromethane in the presence of tetrabutyl-ammonium bromide affords N-tosylsulfoximines 14 ($R^{10}$=p-toluenesulfonyl). The tosyl group of 14 may be removed under acidic conditions, for example, with concentrated sulfuric acid, to give 14 ($R^{10}$= H). Further alkylation, acylation, or sulfonylation of the sulfoximine nitrogen under selected conditions described in the above references then provides additional examples of the sulfoximines 14 which are also antibacterial agents of Formula I claimed in this invention. Representative procedures for converting the sulfoxides 11 into the sulfoximines 14 can be found in the references listed immediately above. For example, 11 can be reacted with O-(mesitylsulfonylhydroxylamine) in a suitable solvent such as dichloromethane, as described in Johnson, C. R. et al., *J. Org. Chem.* 1974, 39, 2458–2459, to furnish the corresponding sulfoximines 14 ($R^{10}$=H). Functionalization of the sulfoximine nitrogen as described above affords additional examples of 14. Alternatively, 11 can be reacted with p-toluenesulfonyl azide in the presence of a suitable promoter such as Raney copper and in a suitable solvent such as methanol or methanol/dichloromethane, as described in Johnson, C. R. et al., *J. Am. Chem. Soc.* 1973, 95, 4287–4291, to provide the N-tosylsulfoximines 14 ($R^{10}$= p-toluenesulfonyl). As described above, the tosyl group may be removed and replaced with alternative groups to give additional examples of sulfoximines 14.

It will be apparent to those skilled in the art that the described synthetic procedures are merely representative in nature and that alternative conditions are known, for example, substituted morpholines where $R^1$ is not equal to hydrogen: Araki, K. et al., poster presented at the 28th Interscience Conference on Antimicrobial Agents and Chemotherapy, Oct. 23–26, 1988, Los Angeles, Calif., Abstract No. 947; and JP 03,291,274, JP 03,148,276, JP 03,066,688, JP 03,048,682, JP 02,019,380, JP 02,115,182, and EP 311,948. Synthesis of substituted hexahydro-1,4-oxazepine where $R^1$ is not equal to hydrogen can be followed from Araki, K. et al., JP 02,115,181. For n is 0, see, Oh, Chang-Hyun et al., J.Antibiotics, 47:126–28 (1994).

These compounds are useful for treatment of microbial infections in humans and other warm blooded animals such as cattle by either parenteral, oral, or topical administration. An example, where the subject invention would be useful in cattle is in the treatment of mastitis.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting bacterial infections in patients such as humans and other animals that can be diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (add addition salt or base salt) dissolved in a pharmaceutically acceptable liquid carrier such as, for example, water-for-injection and a buffer to provide a suitably buffered isotonic solution, for example, having a pH of about 3.5–7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

Antimicrobial activity was tested in vivo using the Murine Assay procedure. Groups of female mice (six mice of 18–20 grams each) were injected intraperitoneally with *Staphylococcus aureus* bacteria which were thawed just prior to use and suspended in brain heart infusion with 4% brewers yeast (*Staphylococcus aureus*) or brain heart infusion (Streptococcus species). Antibiotic treatment at six dose levels per drug was administered one hour and five hours after infection by either oral intubation or subcutaneous routes. Survival was observed daily for six days. $ED_{50}$ values based on mortality ratios were calculated using probit analysis. The subject compounds were compared against vancomycin as a control. The data are shown in Table 1.

TABLE 1

In Vivo Activity of Examples 1–5 Against
*S. aureus* UC ® No. 9213

| Example No. | $ED_{50}$ (mg/kg) | |
|---|---|---|
| | Example, PO | Vancomycin, SC |
| 1 | 1.25 | 3.9 |
| 2 | 2.0 | 2.3 |
| 8 | 3.4 | 2.5 |
| 4 | 5.5 | 2.0 |
| 5 | 5.6 | 3.9 |
| 8 | 12.4 | 2.0 |
| 9 | 4.4 | 2.0 |
| 10 | 6.8 | 5.0 |
| 11 | 14.0 | 2.0 |

TABLE 2

In Vitro Activity Against *M. tb* and *M. avium*

| COMPOUND EXAMPLE NO. | MICA *M. tuberculosis* 91-2225[B] | MIC[A] *M. avium* Lowell Young | MIC[A] *M. avium* LPR |
|---|---|---|---|
| 1 | 0.5 | 1.0 | 4.0 |
| 2 | 0.5 | 2.0 | 4.0 |
| ISONIAZID[C] | ≦0.015 | Not done | Not done |
| AZITHROMYCIN[C] | Not done | 4.0 | 8.0 |

[A]The lowest concentration of drug required to kill the organism or inhibit its growth in vitro.
[B]Strain designation
[C]Isoniazid is a control drug for the tuberculosis test and azithromycin is a control drug for the *mycobacterium avium* test.

The in vitro activity reported in Table 2 was conducted by standard dilution methods known to those skilled in the art. Briefly, serial two-fold dilutions of antibiotic are prepared in a diluent, and a standard volume of mycobacterial growth medium is added to drug aliquot. The medium is inoculated with a standardized mycobacterial cell suspension, and then incubated under appropriate conditions.

Following incubation, the Minimal Inhibitory Concentration (MIC) is determined by visual observation. The MIC is defined as the lowest drug concentration (in µg/ml) required to inhibit mycobacterial growth.

TABLE 3

In vivo Antimycobacterial Activity

| COMPOUND EXAMPLE NO. | $Log_{10}$ Colony-Forming Units of *Mycobacterium tuberculosis* Per Organ[A] | |
|---|---|---|
| Drug Treatment | Spleen | Lung |
| None[B] | 7.72 | 8.47 |
| Isoniazid[C] | 4.36 | 3.81 |
| 4 | 5.24 | 5.03 |
| 1 | 4.61 | 3.59 |

[A]Organ-count enumeration of viable *M. tuberculosis* was conducted following 1 month therapy of infected mice.
[B]Infected but not treated animals which served as the negative (untreated) control.
[C]Isoniazid (positive control drug) was dosed at 25 mg/kg orally while the three test drugs were dosed at 100 mg/kg.

The in vivo data for Table 3 was obtained from CD-1 mice infected intravenously with $1 \times 10^7$ viable *M. tuberculosis*

(Erdman strain). Twenty-four hours later drug treatment was initiated. All the drugs were given by oral gavage twice daily for four weeks. At the end of therapy, viable cell counts were determined from homogenates of spleens and lungs.

EXAMPLE 1

(S)-N-[[3-[3-fluoro-4-(4-thiomorpholinyl)phenyl]-2-oxo-5-oxazolidinyl] methyl]acetamide Step 1: 4-(2-fluoro-4-nitrophenyl)thiomorpholine The 3,4-difluoronitrobenzene (2.09 mL, 18.857 mmol) was dissolved in dry $CH_3CN$ (50 mL) and then treated dropwise with N,N-diisopropylethyl amine (8.212 mL, 47.143 mmol). The resultant yellow mixture was next treated with thiomorpholine (4.74 mL, 47.143 mmol). The reaction was heated to roflux (85° C.) for 16 hours and then it was allowed to cool to ambient temperature over 3 hours, stirring under $N_2$. At this point, the reaction was determined to be complete by TLC (15% EtOAc/hexane, UV short wave). The reaction mixture was first concentrated under reduced pressure and then adsorbed onto silica gel (50 g). The material was chromatographed on more silica gel (175 g, packed with hexane), eluting with 1 L each of 5%, 10% and 15% EtOAc/hexane to give 4.6 g (100%) of the title compound as an orange, crystalline solid with a melting point of 59.5°–60.5° C. and a HRMS ($M^+$) calculated for $C_{10}H_{11}N_2O_2FS$ 242.0522, found 242.0525.

Step 2: 4-[2-fluoro-4-(benzyloxycarbonyl)aminophenyl] thiomorpholine

The 4-(2-fluoro-4-nitrophenyl)thiomorpholine (3.67 g, 8.255 mmol) was dissolved in THF (75 mL) and then treated with a solution of sodium hydrosulfite (26.4 g, 151.56) in water (150 mL). The reaction was slightly exothermic. After an hour, the reaction was found to be complete by TLC (30% EtOAc/hexane, UV short wave). After cooling to 0° C. in an ice bath, the reaction was quenched with $NaHCO_3$ (25.5 g, 303.12 mmol). Next, the reaction was diluted with pH 7 buffer (500 mL). After this solution was saturated with solid NaCl, the product was extracted into $CH_2Cl_2$ (4×500 mL). The combined extracts were dried over anhydrous $Na_2SO_4$, filtered and then concentrated under reduced pressure to yield a yellow solid that was stored in the freezer overnight (16 hours). The crude amine (1.826 g, 8.601 mmol) was dissolved in dry THF (85 mL) and then cooled to −20° C. (MeOH/ice bath). The solution was treated with N,N-dimethylaniline (1.36 mL, 10.75 mmol) and then allowed to stir at −20° C. for 15 minutes. Next, benzylchloroformate [1.42 mL (corrected for 95% purity), 9.46 mmol] was added dropwise. A precipitate fomed almost immediately. The reaction was allowed to stir for an additional 15 minutes before the bath was removed. Upon warming to room temperature under $N_2$ (1 hour), the reaction was found to be complete by TLC (30% EtOAc/hexane, UV short wave). The reaction was diluted with EtOAc (200 mL) and then washed with both water (2×200 mL) and brine (200 mL). The aqueous portions were combined and then back-extracted with more EtOAc (2×200 mL). The organic portions were combined, dried over anhydrous $Na_2SO_4$, filtered and concentrated under reduced pressure to yield a yellowish solid. This crude material was chromatographed on silica gel (150 g, packed with 5% EtOAc/hexane), eluting with 2 L of 5% EtOAc/hexane, 1 L of 10% EtOAc/hexane ($CH_2Cl_2$ was added to maintain solubility) to give 2.65 g (50%) of the title compound as an off-white crystalline solid with a melting point of 142° C. and a HRMS ($M^+$) calculated for $C_{18}H_{19}N_2O_2FS$ 346.1151, found 346.1157.

Step 3: (R)-[3-[3-fluoro-4-(4-thiomorpholinyl)phenyl]-2-oxo-5-oxazolidinyl]methanol The 4-[2-fluoro-4-(benzyloxycarbonyl)aminophenyl] thiomorpholine (2.0 g, 5.77 mmol) was dissolved in dry THF (55 mL) and then cooled to −78° C. (dry ice/acetone bath). This solution was treated with the dropwise addition of n-butyllithium over 6 minutes. The mixture was stirred at −78° C. for 30 minutes and then treated with (R)-(−)-glycidylbutyrate (0.85 mL, 6.0 mmol) dropwise over 2 minutes. The reaction was stirred at −78° C. for an additional 30 minutes before the ice bath was removed. The reaction was allowed to warm to ambient temperature, stirring under $N_2$ overnight (16 hours). At this time, the reaction was determined to be complete by TLC (5% $MeOH/CHCl_3$, UV short wave). The reaction was diluted with $CH_2Cl_2$ (250 mL) and then washed with both water (3×200 mL) and brine (200 mL). The aqueous portions were then back-extracted with more $CH_2Cl_2$ (3×150 mL). The organic portions were combined, dried over snhydrous $Na_2SO_4$, filtered and concentrated under reduced pressure to yield a yellow solid. This crude material was chromatographed on silica gel (175 g, packed with 10% $CH_3CN/CHCl_3$), eluting with a gradient of 1–3% MeOH in 10% $CH_3CN/CHCl_3$ to give 1.583 g (88%) of the title compound as an off-white solid with a melting point of 136°–137° C. and a HRMS ($M^+$) calculated for $C_{14}H_{17}N_2O_3FS$ 312.0944, found 312.0942.

Step 4: (R)-[[3-[3-fluoro-4-(4-thiomorpholinyl)phenyl]-2-oxo-5-oxazolidinyl]methyl]-p-toluenesulfonate The [3-[3-fluoro-4-(4-thiomorpholinyl)phenyl]-2-oxo-5-oxazolidinyl]methanol (1.465 g, 4.69 mmol) was dissolved in pyridine (15 mL) and then cooled to 0° C. (ice bath). This solution was next treated with p-toluenesulfonyl chloride (1.34 g, 7.035 mmol) and allowed to stir at 0° C. under $N_2$ for 7 hours. At this point, the reaction was stoppered and stored in the freezer overnight (16 hours). In the morning, the reaction showed only a trace of starting material by TLC (5% $MeOH/CHCl_3$, UV short wave). The product was precipitated by quenching the reaction mixture with ice water (100 mL). The solid was isolated by suction filtration and washed thoroughly with water. The title compound, 2.02 g (92%), was recovered as a white solid with a melting point of 141° C. and a HRMS ($M^+$) calculated for $C_{21}H_{23}N_2O_5FS_2$ 466.1032, found 466.1036.

Step 5: (R)-[[3-(3-fluoro4-(4-thiomorpholinyl)phenyl]-2-oxo-5-oxazolidinyl]methyl]azide The [[3-[3-fluoro-4-(4-thiomorpholinyl)phenyl]-2-oxo-5-oxazolidinyl]methyl]-p-toluenesulfonate (2.0 g, 4.287 mmol) was dissolved in dry DMF (15 mL) and then treated with solid $NaN_3$ (1.67 g, 25.722 mmol). The reaction was heated to 65° C. (external temperature) for 6 hours, after which the reaction was allowed to cool to ambient temperature, stirring over a long weekend (158 hours). At this point, the reaction was found to be complete by TLC (6% $CH_3CN/CHCl_3$, UV short wave). The reaction was diluted with EtOAc (300 mL) and then washed with water (3×250 mL). The aqueous portions were back-extracted with more EtOAc (2×150 mL). The EtOAc portions were combined, dried over $Na_2SO_4$, filtered and concentrated under reduced pressure to give 1.447 g (100%) of the title compound as an off-white solid with a melting point of 91.5°–93° C. and a HRMS ($M^+$) calculated for $C_{14}H_{16}N_5O_5FS$ 337.1009, found 337.1009.

Step 6: (S)-N-[[3-[3-fluoro-4-(4-thiomorpholinyl)phenyl]-2-oxo-5-oxazolidinyl]methyl]acetamide The crude [[3-[3-fluoro-4-(4-thiomorpholinyl)phenyl]-2-oxo-5-oxazolidinyl]methyl]azide (889 mg, 2.635 mmol) was dissolved in dry THF (15 mL) and treated with triphenylphosphine (864 mg, 3.294 mmol). After an hour, the reaction was found to be complete by TLC (10% MeOH/CHCl$_3$, UV short wave). Next, water (0.949 mL, 52.7 mmol) was added and the reaction was heated to 50° C. for two hours. At this point, the reaction was incomplete; so more water (0.475 mL, 26.35 mmol) was added and the reaction was heated to 60° C. for 5 hours. The reaction was then allowed to cool to ambient temperature, stirring overnight (11 hours) under N$_2$. In the morning, the reaction was found to be complete by TLC (10% MeOH/CHCl$_3$, UV short wave). The reaction was concentrated and then dried under high vacuum for two hours. Next, the semi-solid was dissolved in CH$_2$Cl$_2$ (15 mL) and treated with pyridine (0.320 mL, 3.953 mmol). The reaction was allowed to stir for 15 minutes and then the acetic arthydride (0.497 mL, 5.270 mmol) was added dropwise. After an hour, the reaction was complete by TLC (10% MeOH/CHCl$_3$, UV short wave). The reaction mixture was diluted with CH$_2$Cl$_2$ (50 mL) and then washed with 1 N HCl (50 mL), saturated NaHCO$_3$ (50 mL), and brine (50 mL). Each aqueous portion was back-extracted with more CH$_2$Cl$_2$ (2×20 mL each). The organic portions were combined, dried over anhydrous Na$_2$SO$_4$, filtered and concentrated under reduced pressure to yield a white solid. This crude material was chromatographed on silica gel (100 g, packed with 10% CH$_3$CN/CHCl$_3$), eluting with 1–2% MeOH in 10% CH$_3$CN/CHCl$_3$ to give 667 mg (72%) of the title compound as a white solid with a melting point of 185.5°–186.5° C. and a HRMS (M$^+$) calculated for C$_{16}$H$_{20}$N$_3$O$_3$FS 353.1209, found 353.1200.

EXAMPLE 2

(S)-N-[[3-[3-fluoro-4-(1,1-dioxothiomorpholin-4-yl) phenyl]-2-oxo-5-oxazolidinyl]methyl]acetamide The N-[[3-[3-fluoro-4-(4-thiomorpholinyl)phenyl]-2-oxo-5-oxazolidinyl]methyl]acetamide (280 mg, 0.792 mmol) was slurried in 25% water/acetone solution (12 mL) and then treated with solid 4-methylmorpholine N-oxide (278 mg, 2.376 mmol). Next, the osmium tetroxide in 2-methyl-2-propanol (0.037 mL of a 2.5% solution, 15%) was added dropwise. The reaction was allowed to stir for 16 hours under N$_2$ at room temperature. At this time, the reaction was determined to be complete by TLC (10% MeOH/CHCl$_3$, UV short wave). The reaction mixture was quenched with saturated sodium bisulfite (15 mL) and then extracted into CH$_2$Cl$_2$ (4×25 mL). The combined organic layers were then washed with more saturated sodium bisulfite (100 mL) and brine (100 mL). These aqueous portions were back-extracted with more CH$_2$Cl$_2$ (2×50 mL). All of the organic layers were combined, dried over anhydrous Na$_2$SO$_4$, filtered and then concentrated under reduced pressure to yield an off-white solid. This solid was adsorbed onto silica gel (2.5 g) and chromatographed on more silica gel (30 g, packed with 10% CH$_3$CN/CHCl$_3$), eluting with a gradient of 1–5% MeOH in 10% CH$_3$CN/CHCl$_3$ to give 224 mg (73%) of the title compound as a white solid with a melting point of 202°–203° C. and a HRMS (M$^+$) calculated for C$_{16}$H$_{20}$N$_3$O$_5$FS 385.1108, found 385.1102.

EXAMPLE 3

(S)-N-[[3-[3-fluoro-4-(1-oxothiomorpholin-4-yl)phenyl]-2-oxo-5-oxazolidinyl]methyl]acetamide Sodium metaperiodate (42 mg, 0.196 mmol) was dissolved in water (1 mL) and then cooled to 0° C. (ice bath). Next, the N-[[3-[3-fluoro-4-(4-thiomorpholinyl) phenyl]-2-oxo-5-oxazolidinyl]methyl]acetamide (66 mg, 0.187 mmol) was added. Methanol (3 mL) was added to increase solubility. The reaction was stirred at 0° C. for an additional 4 hours under N$_2$ before being stoppered and stored in the freezer (65 hours). The reaction was filtered through a medium-porosity sintered glass funnel, rinsing the flask and filter cake with CHCl$_3$ (5 mL). The filtrate was transferred to a separatory funnel, the layers separated, and the water layer further extracted with more CHCl$_3$ (3×5 mL). The organic layers were combined, dried over anhydrous Na$_2$SO$_4$, filtered and then concentrated under reduced pressure to yield 80 mg of a gummy solid. The material was chromatographed on silica gel (10 g silica, packed with 10% CH$_3$CN/CHCl$_3$), eluting with a gradient of 1–5% MeOH in 10% CH$_3$CN/CHCl$_3$ to give 49 mg (71%) of the title compound as an off-white solid with amp of 159°–161° C. and a HRMS (M$^+$) calculated for C$_{16}$H$_{20}$N$_3$O$_4$ FS 369.1158, found 369.1182.

EXAMPLE 4

(S)-N-[[3-[3,5-difluoro-4-(4-morpholinyl)phenyl]-2-oxo-5-oxazolidinyl]methyl]acetamide Step 1: 3,5-difluoro-4-morpholinyl-nitrobenzene To a solution of 1.468 g of morpholine and 3.0 mL of diisopropylethylamine in 80 mL of acetenitrile was added a solution of 5.019 g of 2,6-difluoro-4-nitrobenzene (trifluoromethane) sulfonate in 10 mL of acetonitrile. The mixture was heated to reflux for 5 hours, then cooled and concentrated in vacuo. The residue was purified on a silica gel column (3 cm tall, 10 cm diam), eluting with 25% ethyl acetate/hexanes (v/v) and then 2% acetic acid/25% ethyl acetate/hexanes to give 1.95 g of an orange oil. This was washed with 5% ethyl acetate/hexanes, and the bright yellow solids air dried, mp 91°–92° C.

Step 2: 3,5-difluoro-4-morpholinyl-aniline

A flask containing a solution of 0.203 g of 3,5-difluoro-4-morpholinyl-nitrobenzene in 5 mL of ethyl acetate was alternately evacuated and filled with nitrogen three times, then 50 mg of 105 palladium on carbon was added and the flask again evacuated and filled with nitrogen then with hydrogen via a balloon (three times). The mixture was stirred at 20° C. for a total of 2 hours, then filtered over diatomaceous earth and concentrated in vacuo to give an off-white solid, Rf=0.24 (25% ethyl acetate/hexanes, v/v).

Step 3: N-carbobenzyloxy-3,5-difluoro-4-morpholinyl aniline

To a solution of 0.518 g of 3,5-difluoro-4-morpholinyl-aniline and 0.432 g of sodium bicarbonate in 20 mL of acetone:water (2:1 v/v) at 0° C. was added 0.36 mL of benzyl chloroformate over 2 minutes. After 5.5 hours, the mixture was allowed to warm to ambient temperature and after an additional 2.6 hours, the mixture was added to 25 mL of ethyl acetate and 20 mL of brine. The aqueous layer was extracted with 3×25 ml of ethyl acetate and the combined organic layers were dried (MgSO$_4$), and concentrated in vacuo to give a solid, mp=131°–133° C.

Step 4: (R)-N-[[3-[3,5-difluoro-4-morpholinyl]phenyl]-2-oxo-5-oxazolidinyl]methanol To a solution of 0.195 g of N-carbobenzyloxy-3,5-difluoro-4-morpholinyl aniline in 5.0 mL of freshly distilled tetrahydrofuran at −78° C. under nitrogen was added 0.36 mL of 1.6M n-butyl lithlum/hexane and the mixture stirred for 1.5 hours. At that time 0.10 mL of (R)-glycidyl butyrate was added, and after one hour, the flask was removed from the dry ice bath, and allowed to come to ambient temperature. After an additional 2 hours, to the solution was added 2 mL of saturated aqueous ammonium chloride and 5 mL of ethyl acetate, then enough water to make the aqueous layer homogeneous. The separated aqueous layers were extracted with ethyl acetate, then dried (MgSO₄) and concentrated in vacuo to give a yellow solid. This residue was chromatographed on a 24 cm×2.5 cm column of silica gel 40–63 μm, eluting with a gradient of ethyl acetate/hexane (50%–100%), then with 10–20% methanol/ethyl acetate, to give a white solid, mp=123°–125° C.

Step 5: R-N-[[3-[3,5-difluoro-4-morpholinyl]phenyl]-2-oxo-5-oxazolidinyl]methanesulfonate To a solution of 0.097 g of (R)-N-[[3-[3,5-difluoro-4-morpholinyl]phenyl]-2-oxo-5-oxazolidinyl]methanol and 0.10 mL of triethylamine in 5.0 mL of methylene chloride at 0° C. was added 0.030 mL of methanesulfonyl chloride, and after 30 minutes, the flask was removed from the ice bath and allowed to come to ambient temperature. The mixture was concentrated in vacuo, and partitioned between water and ethyl acetate, and the aqueous layer extracted with ethyl acetate, and the combined organic layers were dried (MgSO₄) and concentrated in vacuo to give a white solid, Rf=0.55 (ethyl acetate).

Step 6: (R)-N-[[3-[3,5-difluoro-4-morpholinyl]phenyl]-2-oxo-5-oxazolidinyl]methyl]azide To a solution of (R)-N-[[3-[3,5-difluoro-4-morpholinyl]phenyl]-2-oxo-5-oxazolidinyl]methanesulfonate (0.082 g) in 3.0 mL of dimethylformamide was added 0.069 g of sodium azide, and the mixture heated at 60° C. overnight. The mixture was cooled and concentrated in vacuo, maintaining the apparatus behind a safety shield, to give a white solid. This residue was taken up in water and ethyl acetate and the aqueous layer was extracted three times with ethyl acetate. The combined organic layers were washed with brine, then dried (MgSO₄), and concentrated to give a colorless oil, Rf=0.29 (1:1 v/v ethyl acetate/hexane).

Step 7: (S)-N-[[3-[3,5-difluoro-4-morpholinyl]phenyl]-2-oxo-5-oxazolidinyl]methyl]acetamide The flask containing a solution of 0.632 g of (R)-N-[[3-[3,5-difluoro-4-morpholinyl]phenyl]-2-oxo-5-oxazolidinyl]methyl]azide in 35 mL of ethyl acetate was evacuated and filled with nitrogen (three times). Then 0.116 g of 10% palladium/carbon was added and the flask again evacuated and filled with nitrogen (three times), then with hydrogen from a balloon (three times). The mixture was stirred for 3.3 hours, then evacuated and filled with nitrogen (three times), and 3.0 mL of pyridine and 2.0 mL of acetic anhydride were added. After a period of 40 minutes, the mixture was filtered over diatomaceous earth, and the filtrate concentrated in vacuo overnight. The residue of pink solids was recrystallized from hot ethyl acetate/hexane to give a solid. This was chromatographed on a 2.5 cm×26 cm 40–63 μm silica gel column, eluting with a gradient of 0–10% methanol/ethyl acetate (v/v); the combined proper fractions gave a solid which was triturated with ethyl acetate/hexanes (1:1, v/v) to give a white solid, mp=195°–198° C.

EXAMPLE 5

(S)-N-[[3-[3-fluoro-4-(4-morpholinyl)phenyl]-2-oxo-5-oxazolidinyl]methyl]acetamide Step 1: 3-fluoro-4-morpholinyl-nitrobenzene To a solution of 19.9 g of morpholine, 28.7 g of 3,4-difluoronitrobenzene, and 14.8 g of diisopropyl ethylamine in 100 mL of ethyl acetate was heated at reflux under nitrogen for 4 h. The mixture was allowed to cool to room temperature overnight, then 100 mL of ethyl acetate, 150 mL of methylene chloride, and 150 mL of water were added, and the aqueous layer extracted with 2×50 mL of methylene chloride and 50 mL of ethyl acetate. The combined organic layers were dried (Na₂SO₄) to give a yellow solid. This was recrystallized from acetone-water to give a yellow solid, mp=112°–113° C.

Step 2: 3-fluoro-4-morpholinyl-aniline

To a suspension of 36.56 g of 3-fluoro-4-morpholinyl-nitrobenzene and 48.84 g of ammonium formate in 110 mL of tetrahydrofuran and 440 mL of methanol under nitrogen was added 0.524 g of 10% palladium/carbon. After stirring the mixture for a total of 3 hours, the mixture was filtered through diatomaceous earth, and the filter pad was washed with ethyl acetate. The filtrate was concentrated to a volume of about 450 mL and then 200 mL of water was added. This was extracted with 300 mL of ethyl acetate, then the organic layer was washed with 2×150 mL of water and then 200 mL of brine, dried (MgSO₄), and concentrated to give a brown solid, Rf=0.47 (1:1 ethyl acetate/hexanes, v/v).

Step 3: N-carbobenzyloxy-3-fluoro-4-morpholinyl aniline

To a solution of 28.91 g of 3-fluoro-4-morpholinyl-aniline and 27.88 g of sodium bicarbonate in 500 mL of acetone and 250 mL of water at 0° C. was added 28.68 g of benzyl chloroformate. After stirring the mixture for 1.5 hours, the mixture was poured onto 1000 cc of ice and water, and the ice allowed to melt. The precipitated solid was collected by filtration and washed with 3×250 ml of water, and then dried in a vacuum oven at 75° C. to give a gray-purple solid. This was recrystallized from acetone-water to give a cream-colored solid, mp=123°–124° C.

Step 4: (R)-N-[[3-[3-fluoro-4-morpholinyl]phenyl]-2-oxo-5-oxazolidinyl]methanol

To a solution Of 39.01 g of N-carbobenzyloxy-3-fluoro-4-morpholinyl aniline in 550 mL of freshly distilled tetrahydrofuran at −78° C. under nitrogen was added 77 mL of 1.6M n-butyl lithium/hexane via syringe over 30 minutes, and the mixture stirred for an additional 40 minutes. At that time, a solution of 18.32 g of (R)-glycidyl butyrate in 30 mL of tetrahydrofuran was added over 30 minutes, and after 1.5 hours, the flask was removed from the dry ice bath, and allowed to come to ambient temperature. After stirring the mixture overnight, 20 ml of saturated aqueous ammonium chloride was added, followed by 500 mL of water, and the aqueous layer extracted with ethyl acetate (4×300 mL). The combined organic layers were washed with 200 mL of brine and dried (MgSO₄) to give a light purple solid. This is triturated with 1200 mL of 1:1 ethyl acetate/hexanes (v:v), then recrystallized from ethyl acetate/hexanes to give a white solid, mp=110°–113° C.

Step 5: (R)-N-[[3-[3-fluoro-4-morpholinyl]phenyl]-2-oxo-5-oxazolidinyl]methanesulfonate To a solution of 13.28 g of (R)-N-[[3-[3-fluoro-4-morpholinyl]phenyl]-2-oxo-5-oxazolidinyl]methanol and 8.71 g of triethylamine in 100 mL of methylene chloride at 0° C. under nitrogen was added 7.4 g of methanesulfonyl chloride over 4 minutes. The mixture was allowed to stir at 0° C. for 30 minutes, then allowed to warm to ambient temperature. A white solid was precipitated. Water (175 mL) and 650 mL of methylene chloride and 100 mL of ethyl acetate were added, but the solid did not all dissolve, therefore the mixture was filtered to give a white solid. Additional material was recovered from the filtrate by multiple extraction of the aqueous layer with methylene chloride. The white solid was dried in a vacuum oven, mp=183°–184° C.

Step 6: (R)-N-[[3-[3-fluoro-4-morpholinyl]phenyl]-2-oxo-5-oxazolidinyl]methyl]azide To a solution of (R)-N-[[3-[3-fluoro-4-morpholinyl]phenyl]-2-oxo-5-oxazolidinyl]methanesulfonate (9.05 g) in 200 mL of dimethylformamide was added 6.367 g of sodium azide, and the mixture heated at 85° C. overnight. The mixture was cooled and poured into 500 mL of water and 150 mL of ethyl acetate. The aqueous layer was extracted with 2×75 mL of ethyl acetate, and the combined organic layers were dried (MgSO$_4$), and concentrated by vacuum distillation to remove the bulk of the dimethylformamide. The brown oil, containing some dimethylformamide, was utilized without further purification, Rf=0.74 (10% methanol/ethyl acetate v/v).

Step 7: (S)-N-[[3-[3-fluoro-4-morpholinyl]phenyl]-2-oxo-5-oxazolidinyl]methyl]acetamide A flask containing the crude azide (R)-N-[[3-[3-fluoro-4-morpholinyl]phenyl]-2-oxo- 5-oxazolidinyl]methyl]azide (assume 24.2 mmol) in 500 mL of ethyl acetate was evacuated and filled with nitrogen (three times). Then 0.602 g of 10% palladium/carbon was added and the flask again evacuated and filled with nitrogen (three times), then with hydrogen from a balloon (four times). The mixture was stirred for 17 hours, then a fresh balloon of hydrogen was attached. After a period of 5 hours, the flask was evacuated and filled with nitrogen (three times), and 16 mL of pyridine and 10 mL of acetic anhydride were added. After a period of 2.5 hours, the mixture was filtered over diatomaceous earth, washing the pad with ethyl acetate, and the filtrate concentrated in vacuo to give a brown gummy solid. The residue was purified by chromatography on a 5.5 cm×25 cm 40–63 µm silica gel column, eluting with a gradient of 2–10% methanol/ethyl acetate (v/v); the combined proper fractions gave an off white solid, which was triturated with ethyl acetate and dried to give an off white solid, mp=181.5°–182.5° C.

EXAMPLE 6

(S)-N-[[3-[3-fluoro-4-[1-[(p-toluenesulfonyl)imino]thiomorpholin-4-yl]phenyl]-2-oxo-5-oxazolidinyl]methyl]acetamide The N-[[3-[3-fluoro-4-(4-thiomorpholinyl)phenyl]-2-oxo-5-oxazolidinyl]methyl]acetamide (213 mg, 0.603 mmol) was dissolved in dry CH$_2$Cl$_2$ (11.5 mL) and then treated with hexadecyl-tributylphosphonium bromide (138 mg, 0.271 mmol). To this clear, colorless solution, the chloramine-T (165 mg, 0.723 mmol) was added. The resultant cloudy solution was stirred at room temperature for three hours. At this time, the reaction was determined to be complete by TLC (10% MeOH/CHCl$_3$, UV short wave). The reaction mixture was transferred to a separatory funnel and diluted with CH$_2$Cl$_2$ (10 mL). This solution was washed with cold 5% NaOH (20 mL), water (20 mL), and brine (20 mL). The aqueous portions were combined and then back-extracted with more CH$_2$Cl$_2$ (3×20 mL). The organic layers were combined, dried over anhydrous Na$_2$SO$_4$, filtered and concentrated under reduced pressure. The resultant material was chromatographed on silica gel (100 g), eluting with a gradient of 0–6% MeOH in 10% CH$_3$CN/CHCl$_3$ to give 314 mg (99%) of the title compound as a white solid which decomposes at 79° C. and has a HRMS (FAB) calculated for C$_{23}$H$_{28}$FN$_4$O$_5$S$_2$ (M+H)$^+$, 523.1485, found 523.1477.

EXAMPLE 7

(S)-N-[[3-[3-fluoro-4-4-(3-thiazolidinyl)]phenyl]-2-oxo-5-oxazolidinyl]-methyl]acetamide
Step 1: 3-(2-fluoro-4-nitrophenyl)thiazolidine Using the same general procedure as step 1, of Example 1, 4.092 g (45.90 mmol) thiazolidine was treated with 4.1 mL (37.03 mmol) 3,4-difluoronitrebenzene and 10.0 mL (57.41 mmol) N,N diisopropylethyl amine to provide 2.020 g (24%) of the title compound as an orange solid. Recystallization from methylene chloride/hexane provided an analytical sample with a melting point of 94°–95° C.

Step 2: 3-[2-fluoro-4-(benzyloxycarbonyl)aminophenyl]thiazolidine

The 3-(2-fluoro-4-nitrophenyl)thiazolidine (1.485 g, 6.513 mmool) was dissolved in tetrahydrofuran (25 mL) and water (5 mL) and then shaken under 40 psi of hydrogen in the presence of Raney nickel (500 mg) for 5 hours. After this time, the mixture was filtered over diatomaceous earth. The filter pad was washed with methanol and the filtrate was concentrated to an aqueous layer. Water (15 mL) and acetone (25 mL) were added to the aqueous mixture and the mixture was cooled in an ice bath. Solid sodium bicarbonate (2.728 g, 32.47 mmol) was added followed by benzyl chloroformate (3.0 mL, 21.01 mmol). The mixture was allowed to warm to room temperature and stirred over 3 nights. Ethyl acetate was added to the mixture and the layers were separated. The aqueous layer was extracted with ethyl acetate (3x). The combined organic layers were dried (MgSO$_4$) and concentrated under reduced pressure to provide 3.925 g crude material as a dark oil. The crude was chromatographed on a silica gel column (27 cm×4.5 cm, 40–63µ), eluting with 500 mL 40% hexane/methylene chloride, 1L 20% hexane/methylene chloride, 500 mL 10% hexane/methylene chloride, 500 mL methylene chloride and 500 mL 3% methanol/methylene chloride to provide 480 mg of the title compound as yellow solids and 950 mg of the title compound contaminated with benzyl alcohol. In order to remove the benzyl alcohol contaminate, the contaminated material was treated with triethyl amine (0.6 mL, 4.31 mmol), butyric anhydride (0.45 mL, 2.86 mmol) and a small amount of 4-dimethylamino pyridine at 0° C. After 35 minutes the mixture was concentrated and chromatographed on a silica gel column (23.5 cm×2.5 cm, 40–63µ), eluting with 250 mL 10% ethyl acetate/hexane and 500 mL 15% ethyl acetate/hexane to provide 700 mg of the title compound as light yellow solids. In all, 1.180 g (59%) of the title compound was obtained. Recrystallization from ethyl ether-faexane provided an analytical sample with a melting point of 90°–92° C.

Step 3: (R)-[3-[3-fluoro-4-(3-thiazolidinyl)phenyl]-2-oxo-5-oxazolidinyl]methanol Using the same general procedure as step 3 of example 1, 3-[2-fluoro-4-(benzyloxycarbonyl) aminophenyl]thiazolidine (692 mg, 2.24 mmol) was treated sequentially with n-butyllitium (1.5 mL, 2.40 mmol) and (R)-(−)-glycidylbutyrate (0.33 mL, 2.33 mmol) to provide 500 mg (78%) of the title compound. Recystallization from methylene chloride/hexane provided an analytical sample with a melting point of 96°97° C.

Step 4: (R)-[[3-[3-fluoro-4-(3-thiazolidinyl)phenyl]-2-oxo-5-ozazolidinyl]methyl]-methanesulfonate (R)-[3-[3-fluoro-4-(3-thiazolidinyl)phenyl]-2-oxo-5-oxazolidinyl]methanol (300 mg, 1.05 mmol) and triethylamine (0.30 mL, 2.16 mmol) in 15 mL of methylene chloride was cooled in an ice bath and treated with methanesulfonyl chloride (0.10 mL, 1.29 mmol). The mixture was removed from the ice bath and stirred at room temperature for 45 minutes then 10 mL of 1N HCl was added. The resulting layers were separated and the aqueous layer was extracted with methylene chloride. The combined organic layers were washed with saturated aqueous sodium bicarbonate, dried (MgSO$_4$), and concentrated under reduced pressure to provide 342 mg (87%) of the title compound as a yellow solid, Rf=0.58 (ethyl acetate).

Step 5: (S)-N-[[3-[3-fluoro-4-(3-thiazolidinyl)phenyl]-2-oxo-5-oxazolidinyl]methyl]acetamide The (R)-[[3-[3-fluoro-4-(3-thiazolidinyl)phenyl]-2-oxo-5-ozazolidinyl]methyl]-methanesulfonate (342 mg, 0.910 mmol) was slurried in 5 ml of tetrahydrofuran: isopropanol (1:1) and treated with 5.0 mL of concentrated ammonium hydroxide in a sealed tube at 85°–95° C. for 6 hours. The mixture was then poured into 20 mL water and 20 mL methylene chloride. The layers were separated and the aqueous layer was extracted with methylene chloride (3x). The combined organic layers were washed with brine, dried (MgSO$_4$) and concentrated under reduced pressure to a yellow oil. The crude was taken up in 20 mL methylene chloride and cooled in an ice bath. The mixture was treated with 0.5 mL pyridine and 0.5 mL acetic arthydride and removed from the ice bath. After stirring of 30 minutes at room temperature, the mixture was concentrated under reduced pressure to an oil. The crude was chromatographed on a silica gel column (23 cm×2.5 cm, 40–63µ) eluting with 200 mL 75% ethyl acetate/hexane, 250 mL ethyl acetate and 500 mL 10% methanol/ethyl acetate to provide 190 mg of the title compound as a yellow solid (53% yield from (R)-[3-[3-fluoro-4-(3-thiazolidinyl)phenyl]-2-oxo-5-oxazolidinyl]methanol). Crystallization of the yellow solid from methylene chloride/hexane provided 113 mg of the title compound as a light yellow solid with a melting point of 103°–105° C.

Step 6: (S)-N-[[3-[3-fluoro-4-morpholinyl]phenyl]-2-oxo-5-oxazolidinyl]methyl]-phthalimide The methanesulfonate (of Ex. 5, step 5), (32.559 g, 87.0 mmol of compound from Step 5, above) and potassium phthalimide 32.348 g, 174.6 mmol) were weighed into a flask. Acetonitrile (500 ml) was added, and the mixture was refluxed under nitrogen atmosphere for 2 days, and was stirred at room temperature over the weekend. The reaction mixture, which contained a white precipitate, was filtered. The solid was carefully washed with acetonitrile. The filtrate was then evaporated to give the desired product, as a yellow solid (22.807 g). Because of the poor recovery, the white solid was stirred with 600 ml of acetonitrile overnight. It was then filtered. The solid was again carefully washed with more acetonitrile. The solvent was evaporated to give the desired compound, (7.964 g). This extraction process was repeated and an additional 4.408 g of product was obtained (35.179 g total). The crude material was recrystallized from acetone and water in several batches (13.138 g, boiling, 800 ml acetone, 900 ml water, cooled to room temperature) to give 31.745 g (86%) of the product, as white crystals in "first crops" along with 2.004 g (5%) in "second crops".

Melting Point: 199°≧200° C.

Mass Spectrum: m/e (rel. abundance): 425 (100, M$^+$), 426 (25.6), 186 (23.9), 176 (14.5), 175 (16.4), 160 (27.1), 150 (18.9), 149 (16.1), 148 (11.5), 77 (11.4); exact mass calc'd for C$_{22}$H$_{20}$FN$_3$O$_5$: 425.137. Found: 425.1387.

Analysis calc'd for C$_{22}$H$_{20}$FN$_3$O$_5$: C, 62.11; H, 4.74; N, 9.88. Found: C, 62.06; H, 4.78; N, 9.88.

Specific Rotation: [α]$_D$–57° (c 0.834, CHCl$_3$).

Step 7: (S)-N-[[3-[3-fluoro-4-morpholinyl]-2-oxo-5-oxazolidinyl]methyl]amine

Ethanol (320 ml) and aqueous methylamine (30 ml of 40%, 386.3 mmol) were added to a flask containing the phthalimido oxazolidinone, from Step 6, (27.013 g, 63.5 mmol). The suspension which was placed under nitrogen atmosphere, was heated at 70° C. for 3 hr. and refluxed for 1 hr. A 55 ml aliquot was removed for purification (the remainder was converted to the acetamide U-100766). This was purified in two batches, on a medium pressure silica column (40×63 µ, 4.2 cm×28 cm, packed with 3% methanol/ methylene chloride, eluted with 500 ml 3%, 2000 ml 5%, 1000 ml 10% methanol/methylene chloride, collected 50 ml fractions) to give 3.681 g of the amine, the title compound, as a white solid.

mp 103°–104° C.

Mass Spectrum: m/e (rel. abundance): 295 (100, M$^+$), 237 (8.9), 222 (10.5), 209 (29.4), 164 (28.6), 151 (53.9), 150 (20.5).

Analysis calc'd for C$_{14}$H$_{18}$FN$_3$O$_3$: C, 56.94; H, 6.14; N, 14.23. Found: C, 56.56; H, 6.24; N, 14.05.

Step 8: (S)-N-[[3-[3-fluoro-4-morpholinyl]phenyl]-2-oxo-5-oxazolidinyl]-methyl]benzyloxyacetamide A solution of the aminomethyl oxazolidinone, from Step 7, (0.201 g, 0.68 mmol) in 5 ml of pyridine was cooled to 0° C. under nitrogen atmosphere. Then benzyloxyacetyl chloride (0.13 ml, 0.82 mmol) was added v/a syringe. The reaction mixture was stirred for 24 hr as it gradually warmed to ambient temperature. The solvent was then evaporated and the residue was purified on a medium pressure silica column (43×60 µ, 2.4 cm×26 cm, packed with 5% methanol/ methylene chloride, eluted with 5% and 10% methanol/ methylene chloride, 15 ml fractions were collected) to give 0.296 g (98%) of the improved quality material as a white solid. A portion of this solid (0.053 g) was recrystallized from methylene chloride and hexanes to give 0.036 g of the desired material as white crystals, mp 104.5°–106° C.

Mass Spectrum: m/e (rel. abundance): 443 (100, M$^+$), 399 (14.2), 234 (28.3), 209 (16.8), 196 (10.1), 176 (9.3), 164 (13.2), 150 (10.6), 91 (60.2).

Analysis calc'd for C$_{23}$H$_{26}$FN$_3$O$_5$: C, 62.29; H, 5.91; N, 9.47. Found: C, 62.04; H, 5.93; N, 9.37.

EXAMPLE 8

(S)-N-[[3-[3-fluoro-4-(4-morpholinyl)phenyl]-2-oxo-5-oxazolidinyl]methyl]hydroxyacetamide The benzyloxyacetamidomethyl oxazolidinone, product of Step 8 from Example 7, (0.163 g, 0.37 mmol) was dissolved in ethyl acetate (10 ml) and methanol (1 ml) and was placed under nitrogen atmosphere by alternately evacuating and filling the system with nitrogen 3x. Then 10% palladium on carbon (0.050 g) was added and the system was again evacuated and filled with nitrogen 3x. Hydrogen was then introduced into the system 2x via a hydrogen balloon. The reaction mixture was stirred over a weekend. The reaction mixture was then filtered through diatomaceous earth which was carefully washed with 5% methanol/ethyl acetate. The solvents were evaporated to give 0.120 g of crude material which was purified on a medium pressure silica column (43×60 µ, 1.6 cm×27 cm, packed and eluted with 10% methanol/methylene chloride, collected 10 ml fractions) to give 0.026 g (20%) of the desired product as a white solid, mp 114°–115° C.

Mass Spectrum: m/e (re. abundance): 353 (100, M$^{30}$), 309 (20.7), 234 (28.4), 222 (7.6), 209 (21.8), 196 (10.2), 176 (24.9), 164 (17.4), 151 (14.9), 138 (19.0), 101 (12.5), 56 (16.8), 43 (18.0).

TLC: 10% Methanol/Methylene Chloride: R$_f$=0.39.

EXAMPLE 9

(S)-N-[[3-[3-fluoro-4-(4-morpholinyl)phenyl]-2-oxo-5-oxazolidinyl]methyl]formamide Acetic anhydride (0.35 ml, 3.7 mmol) was added to a formic acid (2 ml, 53 mmol) solution of the aminomethyl oxazolidinone, product of Step 7 from Example 7, (0.199 g, 0.67 mmol). This solution was stirred under nitrogen atmosphere for two weeks. Then, although there was still evidence of starting material by TLC, the reaction mixture was evaporated. The residue was purified on a medium pressure silica column (43×60μ, 2.4 cm×25 cm, packed and eluted with 5% methanol/methylene chloride, 15 ml fractions were collected) to give 0.162 g (74%) of the desired material as a white foamy solid, mp 44°–47° C.

Mass Spectrum: m/e (rel. abundance): 323 (100, M$^+$), 279 (5.9), 265 (6.7), 234 (11.1), 221 (6.5), 209 (6.8), 176 (13.2), 164 (8.3), 151 (13.0), 138 (8.6).

EXAMPLE 10

(S)-N-[[3-[3-fluoro-4-(4-morpholinyl)phenyl]-2-oxo-5-oxazolidinyl]methyl]methylcarbamate A methylene chloride solution (2 ml) of the aminomethyl oxazolidinone, product of Step 7 from Example 7, (0.209 g, 0.71 mmol) was cooled to 0° C. under nitrogen atmosphere. Triethylamine (0.12 ml, 0.86 mmol) and methyl chloroformate (0.25 ml, 3.23 mmol) were added. The reaction mixture gradually warmed to ambient temperature. After stirring 4.5 hr, the solvent was evaporated to give a foamy pink solid. This residue was purified on a medium pressure silica column (43×60μ, 2.4 cm×25 cm, packed and eluted with 5% methanol/methylene chloride, collected 15 ml fractions) to give 0.188 g of the desired product as a white solid. The upgraded product was then recrystallized from methylene chloride and hexanes to give 0.168 g (67%) of white crystals, mp 147.5°–148.5° C. Another 0.018 g (7%) of the desired compound was isolated in a subsequent recrystallization.

Mass Spectrum: m/e (rel. abundance): 353 (100, M$^+$), 295 (4.3), 234 (14.6), 222 (6.7), 209 (6.7), 176 (16.6), 164 (14.0), 150 (10.6), 138 (13.7), 114 (4.8), 88 (6.1), 43 (10.9).

Specific Rotation: $[\alpha]_D$–14° (c 0.844, CHCl$_3$).

EXAMPLE 11

(S)-N-[[3-[3-fluoro-4-morpholinyl]phenyl]-2-oxo-5-oxazolidinyl]methyl]dichloroacetamide A methylene chloride solution (2 ml) of the aminomethyl oxazolidinone, product of Step 7 from Example 7, (0.200 g, 0.68 mmol) was cooled to 0° C. under nitrogen atmosphere. Then triethylamine (0.11 ml, 0.79 mmol) was added. Dichloroacetyl chloride (0.11 ml, 1.14 mmol) was then added slowly via syringe over 3 main, some gas evolved. The reaction mixture slowly came to ambient temperature as it stirred overnight. The solvent was evaporated and the residue was purified on a medium pressure silica column (43×60μ, 2.5 cm×27 cm, packed and eluted with 2% methanol/methylene chloride, collected 15 ml fractions) to give 0.140 g (51%) of the desired material as a light tan solid, mp 193°–196° C.

Mass Spectrum: m/e (rel. abundance): 407 (M+2$^+$, 64.9), 405 (M$^+$, 100), 176 (12.3), 164 (18.1), 151 (26.7), 150 (18.7), 149 (17.8), 138 (19.6).

Analysis calc'd for $C_{16}H_{18}Cl_2FN_3O_4$: C, 47.31; H, 4.47; N, 10.34. Found: C, 47.12; H, 4.67; N, 10.20.

Specific Rotation: $[\alpha]_D$–36° (c 0.955, CHCl$_3$).

CHART 1

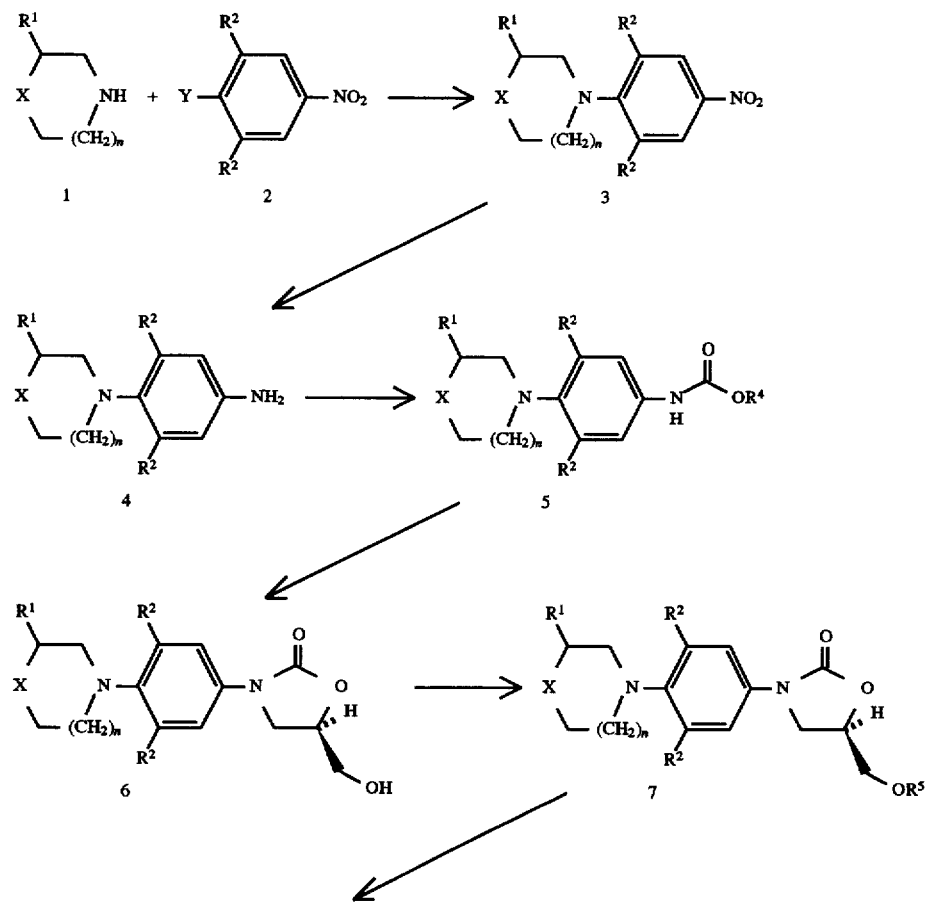

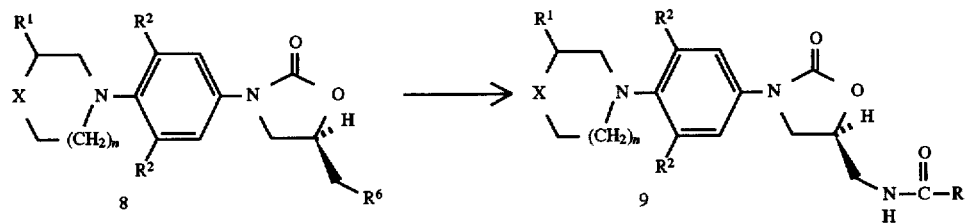
-continued
CHART 1
CHART 2
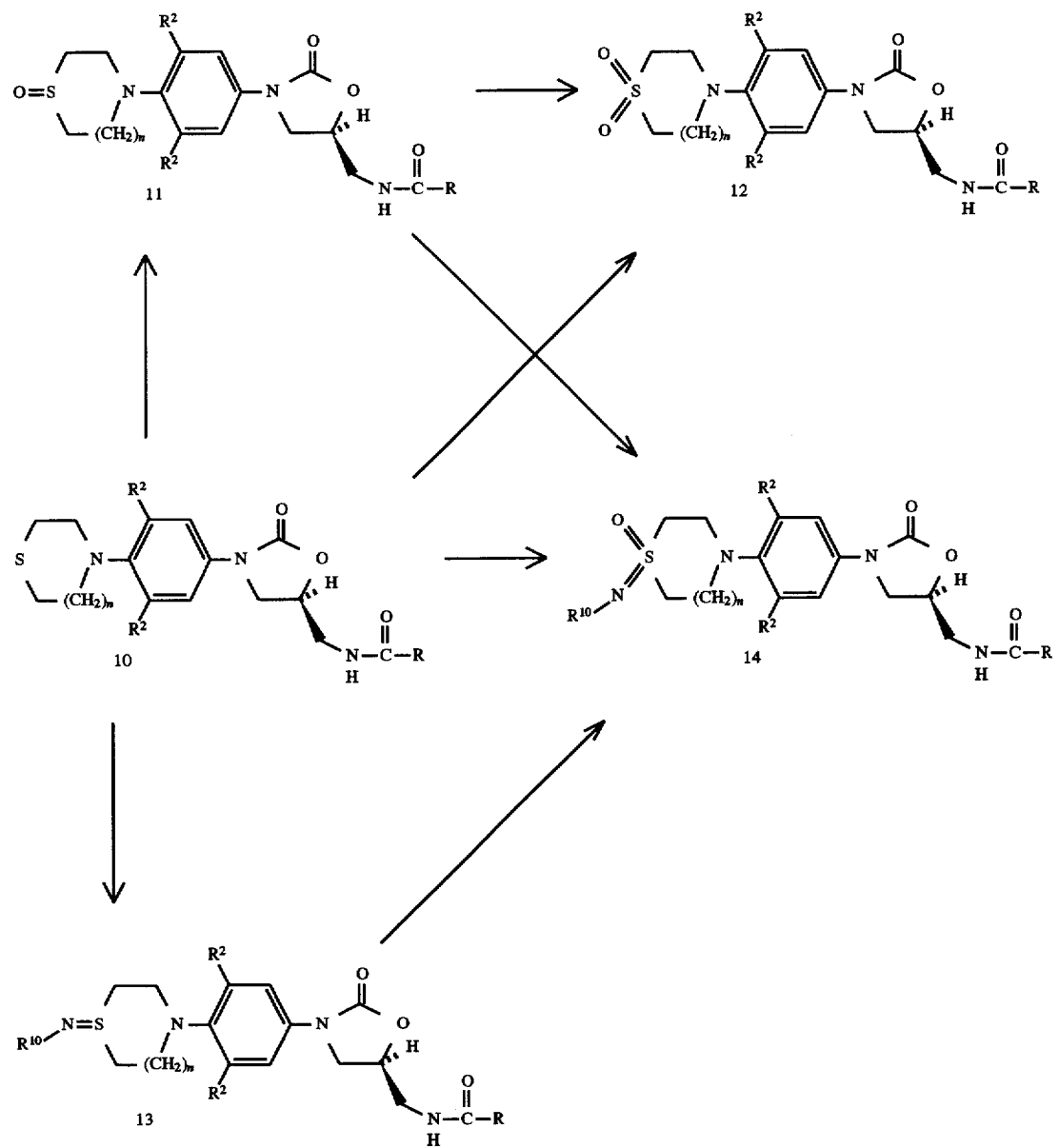

What is claimed:

1. A compound of structural Formula I:

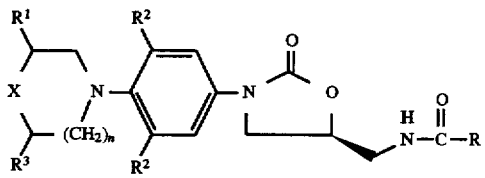

or pharmaceutically acceptable salts thereof wherein:

X is O;

R is (a) hydrogen,
- (b) $C_1$-$C_8$ alkyl optionally substituted with one or more of the following: F, Cl, hydroxy, $C_1$-$C_8$ alkoxy, $C_1$-$C_8$ acyloxy or —O—$CH_2$—Ph,
- (c) $C_3$-$C_6$ cycloalkyl,
- (d) amino,
- (e) $C_1$-$C_8$ alkylamino,
- (f) $C_1$-$C_8$ dialkylamino or
- (g) $C_1$-$C_8$ alkoxy;

$R^1$ is H, $CH_3$, CN, $CO_2H$, $CO_2R$ or $(CH_2)_m R^{11}$ (m is 1 or 2);

$R^2$ is independently H, F or Cl;

$R^3$ is H except when $R^1$ is $CH_3$ then $R^3$ can be H or $CH_3$;

$R^{10}$ is independently H, $C_1$-$C_4$ alkyl (optionally substituted with chloro, fluoro, hydroxy, $C_1$-$C_8$ alkoxy, amino, $C_1$-$C_8$ alkylamino, or $C_1$-$C_8$ dialkylamino) or p-toluenesulfonyl;

$R^{11}$ is hydrogen, OH, OR, OCOR, $NH_2$, NHCOR or $N(R^{10})_2$; and n is 0, 1 or 2.

2. The compound of claim 1 wherein each $R^2$ is fluorine.

3. The compound of claim 1 which is an optically pure enantiomer having the S-configuration at C5 of the oxazolidinone ring.

4. The compound of claim 1 wherein one $R^2$ is hydrogen and the other is fluorine.

5. The compound of claim 1 wherein R is methyl, $OCH_3$, $CHCl_2$, $CH_2OH$ or hydrogen.

6. The compound of claim 1 which is:
- (a) (S)-N-[[3-[3-fluoro-4-(4-thiomorpholinyl)phenyl]-2-oxo-5-oxazolidinyl]methyl]acetamide;
- (b) (S)-N-[[3-[3-fluoro-4-(1,1-dioxothiomorpholin-4-yl)phenyl]-2-oxo-5-oxazolidinyl]methyl]acetamide;
- (c) (S)-N-[[3-[3-fluoro-4-(1-oxothiomorpholin-4-yl)phenyl]-2-oxo-5-oxazolidinyl]methyl]acetamide;
- (d) (S)-N-[[3-[3,5-difluoro-4-(4-morpholinyl)phenyl]-2-oxo-5-oxazolidinyl]methyl]acetamide;
- (e) (S)-N-[[3-[3-fluoro-4-(4-morpholinyl)phenyl]-2-oxo-5-oxazolidinyl]methyl]acetamide;
- (f) (S)-N-[[3-[3-fluoro-4-[1-[(p-toluenesulfonyl)imino]thiomorpholin-4-yl]phenyl]-2-oxo-5-oxazolidinyl]methyl]acetamide;
- (g) (S)-N-[[3-[3-fluoro-4-(4-morpholinyl)phenyl]-2-oxo-5-oxazolidinyl]methyl]hydroxyacetamide;
- (h) (S)-N-[[3-[3-fluoro-4-(4-morpholinyl)phenyl]-2-oxo-5-oxazolidinyl]methyl]formamide;
- (i) (S)-N-[[3-[3-fluoro-4-(4-morpholinyl)phenyl]-2-oxo-5-oxazolidinyl]methyl]methylcarbamate;
- (j) (S)-N-[[3-[3-fluoro-4-(4-morpholinyl)phenyl]-2-oxo-5-oxazolidinyl]methyl]dichloroacetamide.

7. A method useful in treating microbial infections in patients comprising: administering to a patient in need thereof an effective amount of a compound of Formula I as shown in claim 1.

8. The method of claim 7 wherein said compound of Formula I is administered orally, parenterally or topically in a pharmaceutical composition.

9. The method of claim 7 wherein said compound is administered in an amount of from about 0.1 to about 100 mg/kg of body weight/day.

10. The method of claim 9 wherein said compound is administered in an amount of from about 3.0 to about 50 mg/kg of body weight/day.

11. The method of claim 9 wherein said microbial infection is caused by staphylococci, streptococci, enterococci, *Bacteroides spp., Clostridia spp., Mycobacterium tuberculosis, Mycobacterium avium* or *Mycobacterium spp.*

12. The compound of claim 1 which is (S)-N-[[3-[3-fluoro-4-(4-morpholinyl)phenyl]-2-oxo-5-oxazolidinyl]methyl]acetamide.

* * * * *